(12) United States Patent
Honjo et al.

(10) Patent No.: US 7,687,489 B2
(45) Date of Patent: Mar. 30, 2010

(54) AGENT FOR TREATMENT OF CEREBRAL ISCHEMIC DISEASES

(75) Inventors: Kaneyoshi Honjo, Takatsuki (JP);
Narito Tateishi, Mishima-gun (JP);
Nobuo Katsube, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 267 days.

(21) Appl. No.: 11/753,425

(22) Filed: May 24, 2007

(65) Prior Publication Data

US 2007/0219177 A1 Sep. 20, 2007

Related U.S. Application Data

(62) Division of application No. 10/483,629, filed as application No. PCT/JP02/07212 on Jul. 16, 2002, now abandoned.

(30) Foreign Application Priority Data

Jul. 18, 2001 (JP) ............................. P.2001-217755

(51) Int. Cl.
| | | |
|---|---|---|
| *A61K 31/397* | (2006.01) | |
| *A61K 31/20* | (2006.01) | |
| *A61K 31/445* | (2006.01) | |
| *A61K 31/195* | (2006.01) | |
| *A61K 31/40* | (2006.01) | |

(52) U.S. Cl. .................. 514/210.01; 514/558; 514/557; 514/217.12; 514/317; 514/408; 514/237.6; 514/374

(58) Field of Classification Search ........................ None
See application file for complete search history.

(56) References Cited

U.S. PATENT DOCUMENTS 4,029,767 A 6/1977 Vairel et al.
6,201,021 B1 3/2001 Ohuchida et al.

FOREIGN PATENT DOCUMENTS

EP 632008 B1 2/1998
WO 96/15799 A1 5/1996

OTHER PUBLICATIONS

Vippagunta (Adv. Drug Del. Rev., 2001, vol. 48, 2001, pp. 3-26).*
Mark J. Alberts, "Hyperacute stroke therapy with tissue plasminogen actuvatir", The American Journal of Cardiology, 1997, vol. 80 (4C), 29D-39D.
T. Asano et al., "The ameliorative effect of ONO-2506 on the delayed and prolonged expansion cerebral artery occlusion in rates", Journal of Cerebral Blood Flow Metabolism, 1999, vol. 19, Suppl. 1, S64.
Extended European Search Report dated Mar. 19, 2009.
K. Honjo et al., "Effects of ONO-2506 Combined with Thrombolytic Therapy in a Rat Model of Thrombotic Focal Cerebral Ischemia", Society for Neuroscience Abstracts, 2001, p. 2301, vol. 27, No. 2, XP001539303.

* cited by examiner

*Primary Examiner*—Brian-Yong S Kwon
(74) *Attorney, Agent, or Firm*—Sughrue Mion, PLLC

(57) ABSTRACT

A pharmaceutical composition for the treatment and/or prevention of cerebral ischemic diseases, which comprises two components, i.e. an astrocyte function-improving agent, preferably a compound represented by the formula (I):

$$R^5 \diagdown \underset{COR^6}{\overset{(CH_2)_n \diagup R^{11}}{C}} \quad (I)$$

(wherein $R^6$ is hydroxy, etc., (1) n is 1, $R^{11}$ is hydrogen and $R^5$ is (alkyl of which one carbon atom is substituted by fluorine)-$CH_2$— or (2) n is 0 or 1, $R^{11}$ is hydrogen, etc., and $R^5$ is alkyl, etc.) and a thrombolytic agent, preferably tissue plasminogen activator, as active ingredients. The pharmaceutical composition of the present invention exhibits a synergistic therapeutic effect compared to independent administration of an astrocyte function-improving agent and a thrombolytic agent.

2 Claims, No Drawings

AGENT FOR TREATMENT OF CEREBRAL ISCHEMIC DISEASES

This is a divisional of application Ser. No. 10/483,629 filed Jan. 14, 2004, now abandoned which is a National Stage application of PCT Application No. PCT/JP02/07212, filed Jul. 16, 2002, which claims priority of Japanese Application No. JP 2001-217755, filed Jul. 18, 2001, the disclosure of each of which is incorporated herein by reference in its entirety.

FIELD OF THE INVENTION

The present invention relates to a pharmaceutical composition for treating cerebral ischemic diseases. More particularly, the present invention relates to a pharmaceutical composition for the treatment and/or prevention of cerebral ischemic diseases, which comprises two components, i.e. an astrocyte function-improving agent and a thrombolytic agent, as active ingredients.

BACKGROUND OF THE INVENTION

A cerebral ischemic disease is a disorder where necessary blood flow is not supplied to the brain due to thrombus, atherosclerosis, etc. which occurs when blood vessel is obstructed for some reasons, and said ischemic diseases include, for example, cerebral infarction, cerebral hemorrhage, subarachnoid hemmorhage and white matter disorders.

At present, blood flow-improving agents, cerebral metabolism activators, radical scavengers, etc. are used for the treatment of cerebral ischemic diseases. For example, in case of cerebral infarction, the disease can be treated by dissolving generated thrombus and restoring the blood flow again. A thrombolytic agent is usually used for dissolving generated thrombus. As the thrombolytic agent, there has been used tissue plasminogen activator (hereinafter abbreviated as t-PA), urobilinogen (urokinase) and the like (N. Engl. J. Med., 333, 1581 (1995)). However, administration of such thrombolytic agent, particularly t-PA is restricted within 3 hours after occurrence of ischemia, because adverse effects such as bleeding and reperfusion injury (J. Nucl. Med., 41, 1409 (2000) or poor therapeutic effect, etc. would result when administered long after the occurrence of ischemia.

On the other hand, astrocyte function-improving agents have an activity for ameliorating neurological symptoms even quite a long time (24 to 48 hours) after the occurrence of ischemia, but they do not have a thrombolytic activity.

The astrocyte function-improving agents are disclosed, for example, in Japanese Patent Unexamined Publication No. H07-316092 (U.S. Pat. No. 6,201,021), wherein a compound represented by the formula (I):

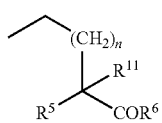

(I)

wherein $R^6$ is hydroxy, C1-4 alkoxy, C1-4 alkoxy substituted by one phenyl group, or $NR^9R^{10}$ in which $R^9$ and $R^{10}$ are independently (i) hydrogen,
(ii) C1-4 alkyl,
(iii) phenyl,
(iv) phenyl substituted by C1-4 alkoxy or carboxy,
(v) 4- to 7-membered heterocycle comprising one nitrogen atom,
(vi) C1-4 alkyl substituted by (a) phenyl, (b) phenyl substituted by C1-4 alkoxy or carboxyl or (c) 4- to 7-membered heterocycle comprising one nitrogen atom,
(vii) 4- to 7-membered heterocycle comprising one or two nitrogen atoms or 4- to 7-membered heterocycle comprising one nitrogen atom and one oxygen atom, when taken together with the nitrogen atom bonded to $R^9$ and $R^{10}$, or
(viii) amino acid residue, when taken together with the nitrogen atom bonded to $R^9$ and $R^{10}$;

n, $R^{11}$ and $R^5$ are (1) n is 1;
  $R^{11}$ is hydrogen;
  $R^5$ is (C1-10 alkyl of which one carbon atom is substituted by one to three fluorine atom)-$CH_2$—, wherein $R^5$ does not represent F—$(CH_2)_5$—, F—$(CH_2)_6$—, F—$(CH_2)_7$— or $F_3C$—$(CH_2)_2$—, or (2) n is 0 or 1;
  $R^{11}$ is hydrogen or chlorine;
  $R^5$ is:
  C3-10 alkyl,
  C3-10 alkenyl,
  C2-10 alkoxy,
  C2-10 alkylthio,
  C3-7 cycloalkyl,
  phenyl,
  phenoxy,
  F—$(CH_2)_m$— (wherein m is an integer of 5 to 7),
  $F_3C$—$(CH_2)_2$—, (C2-10 alkyl substituted by one or two chlorine atom)-$CH_2$—,
  (C1-5 alkyl substituted by one or two substituents selected from the group consisting of C1-4 alkoxy, C3-7 cycloalkyl, phenyl and phenoxy)-$CH_2$—; or
  $R^5$ and $R^{11}$, taken together, are C3-10 alkylidene, is described to possess an activity of improving brain function (especially improvement in astrocyte function) and is useful for the treatment and prevention of Alzheimer's disease, amyotrophic lateral sclerosis, progressive supranuclear palsy, olive-ponto-cerebellar atrophy, neuronal dysfunction by cerebral stroke and traumatic brain injury, multiple sclerosis, astrocytoma, meningitis, brain tumor, Creutzfeldt-Jacob disease, AIDS dementia and the like.

The astrocyte function-improving agent refers to a medicine which is useful for the treatment of diseases resulting from neuron damages by a factor which is released when astrocyte is activated for some reasons. Such an agent has activity for recovering activated astrocyte into normal astrocyte as well as suppressing the activation of astrocyte.

SUMMARY OF THE INVENTION

Based on the facts as mentioned above, the present inventors have studied whether cerebral infarction could be treated by combination use of a thrombolytic agent and an astrocyte function-improving agent. As the result of investigation, it has been found that the astrocyte function-improving agent can synergistically improve survival rate and neurological symptoms with a thrombolytic agent like t-PA without suppressing its thrombolytic activity, and thus said pharmaceutical composition can be used for the treatment of cerebral infarction. The present invention has been completed on the basis of these findings.

That is, the present invention relates to a pharmaceutical composition for treatment and/or prevention of cerebral ischemic diseases, which comprises both an astrocyte function-improving agent and a thrombolytic agent as active ingredients.

The astrocyte function-improving agent used in the present invention includes, for example, a compound represented by the formula (I):

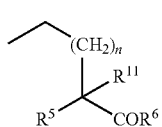

wherein $R^6$ is hydroxy, C1-4 alkoxy, C1-4 alkoxy substituted by one phenyl group, or $NR^9R^{10}$
in which $R^9$ and $R^{10}$ are independently
(i) hydrogen,
(ii) C1-4 alkyl,
(iii) phenyl,
(iv) phenyl substituted by C1-4 alkoxy or carboxyl,
(v) 4- to 7-membered heterocycle comprising one nitrogen atom,
(vi) C1-4 alkyl substituted by (a) phenyl, (b) phenyl substituted by C1-4 alkoxy or carboxyl or (c) 4- to 7-membered heterocycle comprising one nitrogen atom,
(vii) 4- to 7-membered heterocycle comprising one or two nitrogen atoms or 4- to 7-membered heterocycle comprising one nitrogen atom and one oxygen atom, when taken together with the nitrogen atom bonded to $R^9$ and $R^{10}$, or
(viii) amino acid residue, when taken together with the nitrogen atom bonded to $R^9$ and $R^{10}$;
n, $R^{11}$ and $R^5$ are (1) n is 1;
$R^{11}$ is hydrogen;
$R^5$ is (C1-10 alkyl of which one carbon atom is substituted by one to three fluorine atoms)-$CH_2$—, wherein $R^5$ does not represent F—$(CH_2)_5$—, F—$(CH_2)_6$—, F—$(CH_2)_7$— or $F_3C$—$(CH_2)_2$—, or (2) n is 0 or 1;
$R^{11}$ is hydrogen or chlorine;
$R^5$ is:
C3-10 alkyl,
C3-10 alkenyl,
C2-10 alkoxy,
C2-10 alkylthio,
C3-7 cycloalkyl,
phenyl,
phenoxy,
F—$(CH_2)_m$— (m is an integer of 5 to 7),
$F_3C$—$(CH_2)_2$—,
(C2-10 alkyl substituted by one or two chlorine atoms)-$CH_2$—,
(C1-5 alkyl substituted by one or two substituents selected from the group consisting of C1-4 alkoxy, C3-7 cycloalkyl, phenyl and phenoxy)-$CH_2$—, or
$R^5$ and $R^{11}$, taken together, are C3-10 alkylidene, or
a non-toxic salt or hydrate thereof.

Also, the thrombolytic agent used in the present invention includes, for example, tissue plasminogen activator, urobilinogen and the like.

Among the astrocyte function-improving agents used in the present invention, preferred embodiments are (R)-2-propyloctanoic acid and a non-toxic salt or hydrate thereof. Since the compounds represented by the formula (I), in addition to the representative compound, i.e. (R)-2-propyloctanoic acid, have an astrocyte function-improving activity, they are expected well to be effective for cerebral ischemic diseases.

The thrombolytic agents used in the present invention can be exemplified by tissue plasminogen activator (t-PA), urobilinogen and the like, among which tissue plasminogen activator is preferable.

The target diseases of the present invention are cerebral ischemic diseases including cerebral infarction, cerebral hemorrhage, subarachnoid hemorrhage and white matter disorders, etc. The target disease which can be anticipated to be more sensitive is cerebral infarction as proved in the experiments mentioned below.

The present invention includes a method for treating cerebral ischemic diseases by simultaneous administration of an astrocyte function-improving agent and a thrombolytic agent, and also a method for treating cerebral ischemic diseases by administration of a thrombolytic agent, followed by administration of an astrocyte function-improving agent. Since the astrocyte function-improving agent is effective even quite a long time after the occurrence of ischemia and does not suppress thrombolytic activity of the thrombolytic agent, as is apparent from the experiments described hereafter, simultaneous administration is not necessarily required.

The compounds represented by the formula (I) according to the present invention are known per se, or can be prepared according to the methods as described in the specification of Japanese Patent Unexamined Publication No. H07-316092 (U.S. Pat. No. 6,201,021) or WO 00/48982.

The thrombolytic agents used in the present invention are known per se and, for example, t-PA and urobilinogen are commercially available.

The compounds represented by the formula (I) of the present invention may be converted into the corresponding salts by the common method. Non-toxic and water-soluble salts are preferable. Suitable salts include, for example, salts of alkali metals (sodium, potassium, etc.), salts of alkaline earth metals (calcium, magnesium, etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine, etc.), among which sodium salt is particularly preferable.

The compounds represented by the formula (I) of the present invention may be converted into the corresponding acid addition salts by the common method. Non-toxic and water-soluble acid addition salts are preferable. Suitable acid addition salts include, for example, inorganic acid salts (hydrochloride, hydrobromide, hydroiodide, sulfate, phosphate, nitrate, etc.) and organic acid salts (acetate, lactate, tartrate, oxalate, fumarate, maleate, citrate, benzoate, methanesulfonate, ethanesulfonate, benzenesulfonate, toluenesulfonate, isethionate, glucuronate, gluconate, etc.).

The compounds of the formula (I) or salts thereof according to the present invention may be converted into the hydrates by the known method.

Pharmacological Activity of the Pharmaceutical Composition of the Present Invention:

The pharmaceutical composition of the present invention comprising an astrocyte function-improving agent and a thrombolytic agent exhibits effects of improving neurological symptoms, as is apparent from the below-mentioned experiments in cerebral ischemic model, and is, therefore, considered to be effective against cerebral ischemic diseases.

Toxicity:

The toxicity of the astrocyte function-improving agent of the present invention is sufficiently very low and has been confirmed to be safe enough for pharmaceutical use. For example, in the case of single intravenous administration of (R)-2-propyloctanoic acid, among the compounds represented by the formula (I) of the present invention, to dogs, no death was observed at the dose of 100 mg/kg.

Since t-PA is a substance inherent in a living body, no problem would occur unless it is overdosed.

INDUSTRIAL APPLICABILITY

Application to Pharmaceuticals:

The pharmaceutical composition of the present invention comprising an astrocyte function-improving agent and a thrombolytic agent is useful for treatment and/or prevention of cerebral ischemic diseases.

For the above purpose as mentioned above, the agent of the present invention is usually administered systemically or topically in an oral or parenteral dosage form.

Although the dose varies depending on age, body weight, symptom, therapeutic effect, administration route and treatment time, the doses per human adult per dose are generally within a range of 1 mg to 1000 mg, up to several times a day, or within a range of 0.1 mg to 100 mg, up to several times a day, parenteral (preferably intravenous) administration or by continuous intravenous administration over a period of 1 to 24 hours.

As mentioned above, the dose to be prescribed depends upon various conditions, and thus there are cases in which doses lower than or greater than the range as specified above may be required.

When the compounds of the present invention are administered, they are used as solid compositions, liquid compositions or other compositions for oral administration, and as injections, external compositions or suppositories, etc. for parenteral administration.

The solid compositions for oral administration include tablets, pills, capsules, dispersible powders, granules, and the like. The oral compositions also include gargles which are to be stuck to oral cavity and sublingual tablets. The capsules include hard capsules and soft capsules.

In such solid compositions for oral use, one or more of the active compound(s) may be admixed solely or with diluents (such as lactose, mannitol, glucose, microcrystalline cellulose, starch, etc.), binders (such as hydroxypropyl cellulose, polyvinylpyrrolidone, magnesium aluminometasilicate, etc.), disintegrators (such as cellulose calcium glycolate, etc.), lubricants (such as magnesium stearate etc.), stabilizers, solubilizers (such as glutamic acid, aspartic acid, etc.), and then formulated into a preparation in a conventional manner. When necessary, such preparations may be coated with a coating agent such as sucrose, gelatin, hydroxypropyl cellulose, hydroxypropylmethyl cellulose phthalate, etc.) or they may be coated with two or more coating layers. Furthermore, the solid compositions for oral use include capsules of absorbable materials like gelatin.

The liquid compositions for oral administration include pharmaceutically acceptable aqueous solutions, suspensions, emulsions, syrups, elixirs, and the like. In such compositions, one or more of the active compound(s) may be dissolved, suspended or emulsified in a commonly used diluent (such as purified water, ethanol or a mixture thereof, etc.). Besides such diluents, said compositions may also contain wetting agents, suspending agents, emulsifiers, sweetening agents, flavoring agents, perfumes, preservatives and buffers and the like.

Injections for parenteral administration include solutions, suspensions, emulsions, and solid injectable compositions which are dissolved or suspended in a solvent immediately before use. The injections are used by dissolving, suspending or emulsifying one or more of the active compounds in a diluent. Examples of said diluents are distilled water for injection, physiological saline, vegetable oil, alcohol (such as propylene glycol, polyethylene glycol, ethanol, etc.), and a combination thereof. Further, the injections may contain stabilizers, solubilizers (such as glutamic acid, aspartic acid, polysorbate 80 (registered trade mark), etc.), suspending agents, emulsifiers, soothing agents, buffers, preservatives, etc. The injections are sterilized in the final formulation step or prepared by sterile procedure. The injections may also be formulated into sterile solid preparations, for example, by freeze-drying, and may be used after sterilized or dissolved in sterile injectable water or other sterile diluent(s) immediately before use.

DETAILED DESCRIPTION OF THE INVENTION

The following Examples are provided to illustrate the present invention, but are not to be construed as limiting the invention.

Example 1

Effects of the Present Invention in Thrombin-Induced Focal Cerebral Ischemic Model Experiment:

1) Preparation of Ischemic Model

Twenty male Wistar rats (8-weeks age) were used as one group. The rats were anesthetized with halothane, followed by incision and then subjected to carotid artery shunting. A polyethylene catheter containing thrombin (10 international units) was catheterized into the carotid artery, and 10 ml of blood was sucked and reserved in the catheter for 10 minutes. Then, thrombus formed in the catheter was infused into the carotid artery together with thrombin (*J. Cereb. Blood Flow Metab.*, 17, 123 (1997)).

The neurological symptoms of said rats were scored according to the method as described in *Brain Res.*, 452, 323 (1988). The evaluation of score was carried out at 6 hours, 24 hours, 48 hours and 72 hours after infusion of thrombin, and the scores were accumulated. The survival period was determined by monitoring surviving or dead rats at intervals of one hour for the first 72 hours after the infusion of thrombin.

2) Administration of Agent

From forty minutes after thrombin infusion, t-PA (Activacin 100,000 international units, product of Kyowa Hakko Kogyo Co., Ltd.) was continuously administered in an amount of 33 µL/min to the anesthetized rats for 15 minutes. (R)-2-propyloctanoic acid (hereinafter referred to as compound A) in an amount of 10 mg/mL/kg was administered through tail vein of the rats three times at 6 hours, 24 hours and 48 hours after the infusion of thrombin. A physiological saline solution was given to the single drug group and the control group in the same manner, respectively. * indicates that the result is significantly different from the control group (Log-rank test).

Results (Survival Rate):

Survival rate of the rats in thrombin-induced focal cerebral ischemic model at 72 hours after thrombin infusion is given in Table 1.

TABLE 1

| Group | No. of surviving rats | Survival rate after 72 hours |
|---|---|---|
| Control group (Saline) | 6 | 30.0% |
| t-PA administration group | 7 | 35.0% |
| Compound A administration group | 12 | 60.0%*) |
| t-PA and compound A administration group | 14 | 70.0%*) |

*)$p < 0.05$

Consideration (Survival Rate):

As apparent from Table 1, survival rate of the rats when both compounds were administered is higher than that when t-PA or compound A (astrocyte function-improving agent) was solely administered. Especially, it is shown that the number of surviving rats in the group receiving both compounds is two times higher than that of the group receiving only t-PA.

Results (Neurological Defect Score):

The neurological symptom scores in rats of the control group which have survived for 72 hours, t-PA administration group, compound A (astrocyte function-improving agent) administration group, and group of concomitant administration of t-PA and compound A are shown in Table 2. The figure in the table represents average±standard error (Wilcoxon rank sum test). The figure with the symbol * indicates that the result is significantly different from the t-PA administration group, and § indicates that the result is significantly different from the control group.

TABLE 2

| Group | 0 to 6 hours | 0 to 24 hours | 0 to 48 hours | 0 to 72 hours |
|---|---|---|---|---|
| Control group (saline) | 3.3 ± 0.2 | 3.5 ± 0.2 | 3.7 ± 0.2 | 3.5 ± 0.3 |
| t-PA administration group | 3.4 ± 0.2 | 3.4 ± 0.2 | 3.1 ± 0.3 | 3.0 ± 0.3 |
| Compound A administration group | 3.4 ± 0.1 | 3.3 ± 0.1 | 3.3 ± 0.1 | 3.2 ± 0.2 |
| t-PA and compound A administration group | 3.5 ± 0.1 | 2.6 ± 0.2*§ | 2.4 ± 0.3*§ | 2.1 ± 0.3**§ |

*$p < 0.05$,
**$p < 0.01$,
§$p < 0.05$

Discussion (Neurological Symptom Score):

Up to 6 hours of post-infusion of thrombin, there is no difference among the four groups, but after 24 hours, there is a significant improvement in the scores of the concomitant administration group compared to other groups. There is no difference between the group receiving single administration and the control group in all the periods of time, and thus single administration does not improve neurological symptoms at all. These results have revealed that the concomitantly administered agent according to the present invention possesses a synergistic effect on neurological symptoms.

What is claimed is:

1. A method for improving neurological symptoms in focal cerebral ischemia, comprising administering to a mammal suffering from focal cerebral ischemia an effective amount of (R)-2-propyloctanoic acid, or a non-toxic salt thereof, and a tissue plasminogen activator (t-PA).

2. A method for improving neurological symptoms in cerebral infarction, comprising administering to a mammal suffering from cerebral infarction an effective amount of (R)-2-propyloctanoic acid, or a non-toxic salt thereof, and a tissue plasminogen activator (t-PA).

* * * * *